United States Patent [19]

Metz

[11] Patent Number: 4,710,322

[45] Date of Patent: Dec. 1, 1987

[54] PROCESS FOR THE PREPARATION OF ALKALI METAL AND ALKALINE EARTH SALTS OF BENZALDEHYDE-2,4-DI-SULFONIC ACID

[75] Inventor: Hans J. Metz, Heppenheim, Fed. Rep. of Germany

[73] Assignee: Hoechst Aktiengesellschaft, Frankfurt am Main, Fed. Rep. of Germany

[21] Appl. No.: 21,622

[22] Filed: Mar. 2, 1987

Related U.S. Application Data

[63] Continuation of Ser. No. 776,003, Sep. 13, 1985, abandoned.

[30] Foreign Application Priority Data

Sep. 17, 1984 [DE] Fed. Rep. of Germany ....... 3434079

[51] Int. Cl.$^4$ .......................................... C07C 143/38
[52] U.S. Cl. .................................................... 260/511
[58] Field of Search ........................................ 260/511

[56] References Cited

U.S. PATENT DOCUMENTS 1,531,507  3/1925  Rosenbaum ....................... 260/511

FOREIGN PATENT DOCUMENTS 88952  2/1896  Fed. Rep. of Germany .
91818  6/1896  Fed. Rep. of Germany .
98321  1/1897  Fed. Rep. of Germany .

Primary Examiner—Nicky Chan

[57] ABSTRACT

The invention consists in an improved process for the preparation of salts of benzaldehyde-2,4-disulfonic acid from 2,4-dichlorobenzaldehyde. In the process 2,4-dichlorobenzaldehyde is reacted with an aqueous solution of an alkali metal or alkaline earth sulfite and/or hydrogensulfite for a reaction time of less than 7 hours at 140°–180° C. to form the corresponding salt of benzaldehyde-2,4-disulfonic acid with high yield. The product has application in the electroplating industry and in the preparation triphenylmethane dyestuffs.

16 Claims, No Drawings

PROCESS FOR THE PREPARATION OF ALKALI METAL AND ALKALINE EARTH SALTS OF BENZALDEHYDE-2,4-DI-SULFONIC ACID

This application is a continuation of my copending application Ser. No. 776,003, filed Sept. 13, 1985, and now abandoned.

The invention relates to a process for the preparation of alkali metal and alkaline earth salts of benzaldehyde-2,4-disulfonic acid from 2,4-dichlorobenzaldehyde by reaction with an alkali metal or alkaline earth sulfite and/or hydrogensulfite in the presence of water.

Benzaldehyde-2,4-disulfonic acid and its salts constitute valuable technical products and, for example, find application in the electro plating industry or in the production of triphenylmethane dyestuffs.

Essentially two routes are known for the preparation of benzaldehyde-2,4-disulfonic acid and its salts:

(a) side-chain oxidation of toluene-2,4-disulfonic acid by means of manganese salts, (b) reaction of 2,4-dichlorobenzaldehyde with a sulfite and/or hydrogensulfite.

The process described by (a) suffers from the disadvantage of waste water containing heavy metals and loaded with acid and should therefore be avoided if possible.

The state of the art of the process described by (b) is given in the German Reich Patents DRP No. 98,321, DRP No. 91,818 and DRP No. 88,952. Thus, DRP No. 88,952 describes the reaction of 2-chlorobenzaldehyde with an aqueous sodium hydrogensulfite solution in a closed vessel at reaction temperatures of 190°–200°C. and for reaction times of 8 h to form the sodium salt of benzaldehyde-2-sulfonic acid. The sodium salt of 5-chlorobenzaldehyde-2-sulfonic acid is, according to DRP No. 91,818, obtained in an analogous manner from 2,5-dichlorobenzaldehyde. Finally, in DRP No. 98,321 an analogous process is described for the preparation of an aqueous solution of the disodium salt of benzaldehyde-2,4-disulfonic acid from 2,4-dichlorobenzaldehyde at reaction temperatures of 190°–200 C. and for reaction times of 9–10 h. In this case the substance was not isolated and there are no data on yield.

In carrying out the reaction under the conditions specified in the example in DRP No. 98,321, a large proportion of by-products is formed. Dark colored heterogeneous reaction mixtures are obtained, from which the strongly contaminated product can be isolated only with considerable effort with a yield of 30–60% of theory. The objective therefore was to develop a process for the preparation of alkali metal salts of benzaldehyde-2,4-disulfonic acid which provides the desired product at economic yields in a reproducible manner.

It has now been found that, surprisingly, contrary to the teaching of the patents cited above reproducible results with higher yield are obtained if the reaction temperature is below 180° C. It was furthermore surprising that in spite of the low temperature a markedly shorter reaction time than specified in the process of DRP No. 98,321 is advantageous.

The subject of the invention is therefore a process for the preparation of an alkali metal or alkaline earth salt of benzaldehyde-2,4-disulfonic acid from 2,4-dichlorobenzaldehyde by reaction with an alkali metal or alkaline earth sulfite and/or hydrogensulfite in the presence of water, wherein the reaction temperature is 140°–180° C., preferably 160°–170°C., and the reaction time is less than 7 hours, preferably 2–4 hours.

The 2,4-dichlorobenzaldehyde is heated in an expedient manner with an aqueous solution of the sulfite and/or hydrogensulfite of the same cation in a closed vessel while being stirred.

Sulfites and hydrogensulfites of the alkali metals and alkaline earth metals are suitable, particularly those of sodium and potassium. The appropriate concentration of the aqueous solution depends partly on the solubility of the particular sulfites and hydrogensulfites. For example, in the case of sodium sulfi the mass ratio of sulfite to water should preferably be 0.11 to 0.33, and should with particular preference 8 or 0.22–0.25.

The sulfites and/or hydrogensulfites are expediently used in a quantity of 2 to 2.5 mol, preferably 2.05 to 2.15 mol, per mol of 2,4-dichlorobenzaldehyde.

The isolation of the product is carried out in a simple manner after it has crystallized and excess sulfite has been removed. In order to increase the yield it is advantageous to distill off a part of the reaction water first (concentration to 65% of the initial weight is preferable) and then to initiate crystallization by cooling. Excess sulfite can be removed by the usual methods, for example by boiling down with sulfuric acid or by oxidation to sulfate. The preferred method is oxidation with aqueous hypochlorite solution after the crystallization step. The separation of the crystals of the product formed is achieved in a sample manner by centrifuging, but can also be carried out by filtering.

Advantages of the new process compared with the cited state of the art are based on the reproducibility, high yield, saving of energy as a result of the considerably reduced reaction time and the substantially improved space-time yield.

The examples below serve to explain the invention. The percentage figures refer to weight.

EXAMPLE 1

175 g (1 mol) of 2,4-dichlorobenzaldehyde are heated together with a solution of 260 g (2.06 mol) of sodium sulfite in 1100 g of water for 2.5 h at 170° C. Concentration is then carried out to 65% of the initial weight and oxidation is carried out at 5° C. with approx. 200 g of sodium hypochlorite solution (13% NaOCl). 361 g of product is obtained by centrifuging with a content of 73.9% of the disodium salt of benzaldehyde-2,4-disulfonic acid, equivalent to 86% of theory.

EXAMPLE 2

175 g (1 mol) of 2,4-dichlorobenzaldehyde are heated together with a solution of 260 g (2.06 mol) of sodium sulfite in 1190 g of water for 5 h at 170° C. Concentration to 65% of the initial weight is carried out and oxidation is carried out at 5° C. with approx. 200 g sodium hypochlorite solution (13% NaOCl). 310 g of product is obtained by centrifuging with a content of 75.4% of the disodium salt of benzaldehyde-2,4-disulfonic acid, equivalent to 75.4% of theory.

COMPARATIVE EXAMPLE

The procedure is as described in Example 1 except for the following differences. The reaction temperature is kept at 195° C. for 10 h. Before the crystallization step a treatment of the reaction mixture with activated charcoal is necessary. 170 g of product is obtained with a content of approx. 63.5% of the disodium salt of benzaldehyde-2,4-disulfonic acid, i.e. 34.8% of theory, referred to 2,4-dichlorobenzaldehyde.

I claim:

1. A process for the preparation of an alkali metal or alkaline earth metal salt of benzaldehyde-2,4-disulfonic acid, comprising the steps of:

reacting 2,4-dichlorobenzaldehyde with an alkali metal or alkaline earth metal sulfite or an alkali metal or alkaline earth metal hydrogensulfite, or mixtures of any of these salts, in a reaction medium containing water, wherein the reaction temperature is in the range of 140° C. to below 180° C. and the reaction time is less than 7 hours.

2. The process according to claim 1, wherein the reaction temperature is 160°–170° C.

3. The process according to claim 1, wherein the reaction time is 2–4 hours.

4. The process according to claim 2, wherein the reaction time is 2–4 hours.

5. The process according to claim 1, wherein the sulfite and/or hydrogensulfite is used in a quantity of 2–2.5 mols per mol of 2,4-dichlorobenzaldehyde.

6. The process according to claim 2, wherein the sulfite and/or hydrogensulfite is used in a quantity of 2–2.5 mols per mol of 2,4-dichlorobenzaldehyde.

7. The process according to claim 3, wherein the sulfite and/or hydrogensulfite is used in a quantity of 2–2.5 mols per mol of 2,4-dichlorobenzaldehyde.

8. The process according to claim 4, wherein the sulfite and/or hydrogensulfite is used in a quantity of 2–2.5 mols per mol of 2,4-dichlorobenzaldehyde.

9. The process according to claim 1, wherein an aqueous solution of sodium sulfite is used with a mass ratio of sodium sulfite/water of 0.11–0.33.

10. The process according to claim 2, wherein an aqueous solution of sodium sulfite is used with a mass ratio of sodium sulfite/water of 0.11–0.33.

11. The process according to claim 3, wherein an aqueous solution of sodium sulfite is used with a mass ratio of sodium sulfite/water of 0.11–0.33.

12. The process according to claim 4, wherein an aqueous solution of sodium sulfite is used with a mass ratio of sodium sulfite/water of 0.11–0.33.

13. The process according to claim 5, wherein an aqueous solution of sodium sulfite is used with a mass ratio of sodium sulfite/water of 0.11–0.33.

14. The process according to claim 8, wherein an aqueous solution of sodium sulfite is used with a mass ratio of sodium sulfite/water of 0.11–0.33.

15. The process according to claim 2, wherein the reaction time is 2–4 hours and 2.05–2.15 mol of sulfite is used per mol of starting material.

16. Process according to claim 1, wherein the resulting alkali metal of alkaline earth metal salt of benzaldehyde -2,4-disulfonic acid is isolated from the reaction mixture.

* * * * *